United States Patent
Simon

(10) Patent No.: US 6,372,202 B1
(45) Date of Patent: Apr. 16, 2002

(54) COSMETIC COMPOSITION, IN PARTICULAR A MAKE-UP COMPOSITION, COMPRISING A PIGMENT DERIVED FROM PYRROLOPYRROLE

(75) Inventor: Jean-Christophe Simon, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/557,180

(22) Filed: Apr. 21, 2000

(30) Foreign Application Priority Data

Apr. 22, 1999 (FR) .............................. 99 05134

(51) Int. Cl.[7] .................... A61K 7/021; A61K 7/42; A61K 7/04; A61K 7/025; A61K 7/06
(52) U.S. Cl. ..................... 424/63; 424/59; 424/61; 424/64; 424/70.7; 424/70.9; 424/401
(58) Field of Search ............................ 424/401, 59, 63, 424/64, 61, 70.7, 70.9

(56) References Cited

U.S. PATENT DOCUMENTS

| | | |
|---|---|---|
| 4,585,878 A | 4/1986 | Jost et al. |
| 4,666,455 A | 5/1987 | Jost et al. |
| 5,785,750 A | 7/1998 | Hendi |
| 5,786,487 A | 7/1998 | Hendi |
| 5,840,907 A | 11/1998 | Hendi |
| 5,847,156 A | 12/1998 | Eldin et al. |
| 5,919,945 A | 7/1999 | Hendi |
| 5,968,242 A | 10/1999 | Hölderich et al. |
| 6,042,842 A | * 3/2000 | Lemann et al. ............. 424/401 |

FOREIGN PATENT DOCUMENTS

| | | |
|---|---|---|
| EP | 0 133 156 | 2/1985 |
| EP | 0 787 731 A2 | 8/1997 |
| EP | 0 811 625 A2 | 12/1997 |
| EP | 0 849 221 A1 | 6/1998 |

* cited by examiner

Primary Examiner—Jose' G. Dees
Assistant Examiner—Marina Lamm
(74) Attorney, Agent, or Firm—Nixon & Vanderhye P.C.

(57) ABSTRACT

The present invention relates to cosmetic compositions, in particular make-up compositions, comprising an orange pigment with an intense and saturated color which does not generate free radicals. This pigment is a diketodiarylpyrrolopyrrole derivative of formula:

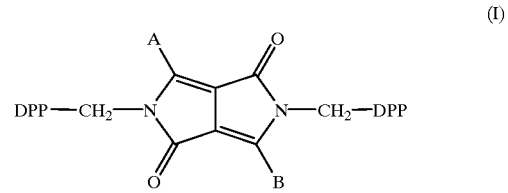

in which A and B are identical or different aryl radicals and DPP is a 1,4-diketo-3,6-diarylpyrrolo[3,4-c]pyrrolidyl radical, the diaryldiketopyrrolopyrrole derivative of formula (I) being substituted by 0 to 6 mol of —$SO_3M$ per mole, M being hydrogen or a metal or ammonium cation.

35 Claims, No Drawings

COSMETIC COMPOSITION, IN PARTICULAR A MAKE-UP COMPOSITION, COMPRISING A PIGMENT DERIVED FROM PYRROLOPYRROLE

The present invention relates to cosmetic compositions comprising a novel orange pigment with an intense and saturated color which does not generate free radicals and more especially to compositions for making up the skin, both of the human face and of the human body, superficial body growths, such as the nails or keratinous fibres, such as the eyelashes, eyebrows or hair, and lips.

Make-up compositions, such as loose or compacted powders, foundations, blushers, eyeshadows, lipsticks, concealers, mascaras, eyeliners, lip pencils, eye pencils or nail varnishes and products for making up the body are composed of an appropriate vehicle and of coloring agents of various natures intended to confer a certain color on these compositions, before and/or after their application to the skin, lips and/or superficial body growths.

These coloring agents can be lakes, inorganic or organic pigments and/or pearlescent pigments, or dyes. In the range of orange pigments, cosmetic technologists have available pigments of inorganic origin, such as brown-yellow iron oxides or mixtures of brown-yellow iron oxides, and pigments of organic origin. Inorganic pigments, in particular inorganic oxides, have the advantage of being very stable but have the disadvantage of giving rather dull and pale colors. Organic lakes have the advantage of conferring vivid colors on the compositions but are generally unstable with regard to light, temperature or pH. Some of these lakes also exhibit the disadvantage of staining the skin in an unsightly way after application by bleeding of the dye. Pearlescent pigments, for their part, make it possible to obtain varied but never intense colors with iridescent but generally fairly weak effects.

Furthermore, some coloring agents exhibit the disadvantage of generating free radicals in make-up formulae, modifying the reproduction of the colors and the stability of the compositions, and then on the skin after application, which promotes cutaneous ageing (appearance of wrinkles, fine lines or yellowing of the skin). Mention may in particular be made, as coloring agents exhibiting this disadvantage, of the mixtures of brown-yellow iron oxides sold under the trade name "Sicomet Brown ZP 3569" by BASF, for example, pigments of organic origin, such as the pigment Orange 5 (CI 12075) or D & C Orange No. 5 (CI 45730:1) or D & C Orange No. 4 (CI 15510), and the aluminium lakes D & C Orange No. 5 Aluminium Lake, D & C Orange No. 4 Aluminium Lake or D & C Orange No. 10 Aluminium Lake.

Today, use is made of antioxidizing agents, such as, for example, ethoxyquin, in order to overcome this disadvantage. Unfortunately, it is often difficult to find an antioxidizing agent which is 100% effective due to the multiplicity of ingredients present in make-up compositions. Furthermore, antioxidizing agents themselves often generate, by oxidation, degradation products which can be a nuisance.

A subject-matter of the present invention is the use, in a cosmetic composition, in particular for obtaining an orange color, of a novel orange pigment with an intense and saturated color which is stable and which has the advantage of generating far fewer free radicals than the pigments conventionally used.

Surprisingly, the Applicant Company has found that some diketodiarylpyrrolopyrrole (abbreviated to DPP) derivatives make it possible to limit the production of free radicals, since they have the property of generating very few free radicals, and thus to avoid the use of antioxidants in the compositions. In addition, these pigments make it possible to obtain an intense and very vivid orange coloring which does not bleed on the skin and which is stable with regard to light, pH and temperature.

More specifically, a subject-matter of the invention is a colored cosmetic composition for topical application and more especially a cosmetic make-up composition comprising a pigment derived from diketodiarylpyrrolopyrrole of formula (I):

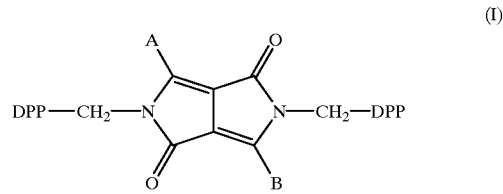

in which A and B are identical or different aryl radicals and DPP is a diketodiarylpyrrolopyrrolidyl radical, the diketodiarylpyrrolopyrrole derivative of formula (I) being substituted by 0 to 6 mol of —$SO_3M$ per mole of pyrrolopyrrole derivative, M being a hydrogen atom or a metal or ammonium cation.

When M is a metal cation, it is preferably a sodium, potassium or lithium cation.

The pyrrolopyrrole derivative of formula (I) is preferably substituted by 0 to 2 mol of —$SO_3M$ and more preferably by 0 to 0.75 mol of —$SO_3M$ per mole of pyrrolopyrrole derivative of formula (I).

Preferred pyrrolopyrrole derivatives do not comprise an —$SO_3M$ radical.

DPP is preferably a 1,4-diketo-3,6-diarylpyrrolo[3,4-c]pyrrolidyl radical of formula:

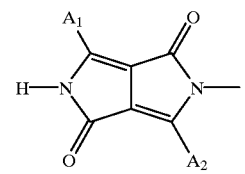

in which $A_1$ and $A_2$ are identical or different aryl radicals.

A, B, $A_1$ and $A_2$ can be aromatic or heteroaromatic radicals.

Particularly appropriate radicals are those of formulae:

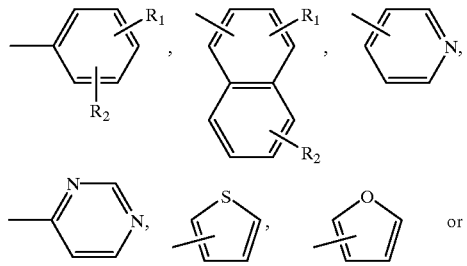

or

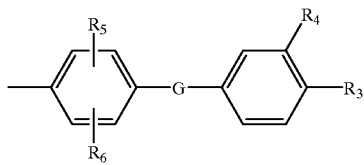

in which:

$R_1$ and $R_2$ denote, independently of one another, a hydrogen or halogen atom or a $C_1$–$C_{18}$ alkyl, $C_1$–$C_{18}$ alkoxy, $C_1$–$C_{18}$ alkylmercapto, $C_1$–$C_{18}$ alkylamino, $C_1$–$C_{18}$ alkoxycarbonyl, $C_1$–$C_{18}$ alkylaminocarbonyl, —CN, —NO$_2$, trifluoromethyl, $C_5$–$C_6$ cycloalkyl, —CH=N—($C_1$–$C_{18}$ alkyl), phenyl,

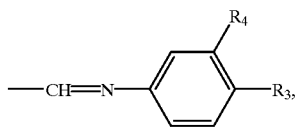

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl radical, G denotes —CH$_2$—, —CH(CH$_3$)—, —C(CH$_3$)$_2$—, —CH=N—, —N=N—, —O—, —S—, —SO—, —SO$_2$—, —CONH— or —NR$_7$—, $R_3$ and $R_4$ denote, independently of one another, a hydrogen or halogen atom or a $C_1$–$C_6$ alkyl, $C_1$–$C_{18}$ alkoxy or —CN radical, $R_5$ and $R_6$ denote, independently of one another, a hydrogen or halogen atom or a $C_1$–$C_6$ alkyl radical, and $R_7$ is a hydrogen atom or a $C_1$–$C_6$ alkyl radical.

In particular, A, B, $A_1$ and $A_2$ each denote a group of formula:

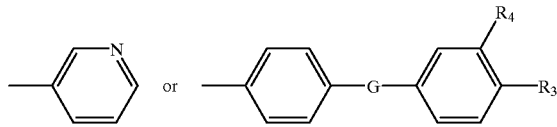

in which:

$R_1$ and $R_2$ each denote, independently of one another, a hydrogen, chlorine or bromine atom or a $C_1$–$C_4$ alkyl, $C_1$–$C_6$ alkoxy, $C_1$–$C_6$ alkylamino, phenyl or —CN radical, G denotes —O—, —NR$_7$—, —N=N— or —SO$_2$—, $R_3$ and $R_4$ denote hydrogen, and $R_7$ is a hydrogen atom or a methyl or ethyl radical.

More particularly, A, B, $A_1$ and $A_2$ each denote a group of formula:

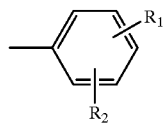

in which:

$R_1$ and $R_2$ each denote, independently of one another, a hydrogen, chlorine or bromine atom or a methyl, tert-butyl, phenyl or —CN radical.

At least one of the $R_1$ and $R_2$ radicals is preferably a hydrogen atom.

More preferably, at least one of the $R_1$ and $R_2$ radicals is a hydrogen atom and the other is in the 3- or 4- position of the phenyl nucleus.

Particularly preferred compounds are those in which A and B are identical and are chosen from the phenyl, 4-methylphenyl, 4-tert-butylphenyl, 4-chlorophenyl, 4-bromophenyl or biphenyl-1-yl (4-phenylphenyl) radicals, especially those in which $A_1$ and $A_2$ are also identical and are chosen from the phenyl, 4-methylphenyl, 4-tert-butylphenyl, 4-chlorophenyl, 4-bromophenyl and biphenyl-1-yl radicals.

A preferred class of pyrrolopyrrole derivatives is that in which $A_1$ and $A_2$ each denote a 4-tert-butylphenyl radical, especially that in which A and B are identical and are chosen from the phenyl, 4-tert-butylphenyl and 4-methylphenyl radicals, preferably the 4-tert-butylphenyl radical.

Thus, a preferred compound according to the invention is the pyrrolopyrrole derivative in which A, B, $A_1$ and $A_2$ each denote a 4-tert-butylphenyl radical.

Another preferred class of pyrrolopyrrole derivatives is that in which $A_1$ and $A_2$ each denote a 4-methylphenyl radical and A and B are identical and are chosen from the phenyl, 4-tert-butylphenyl and 4-methylphenyl radicals, preferably the 4-tert-butylphenyl radical.

The preparation of the diketodiarylpyrrolopyrroles of formula (I) is disclosed in particular in U.S. Pat. No. 5,786,487.

Use is preferably made of the 1,4-diketo-3,6-diphenylpyrrolo[3,4-c]pyrrole derivatives exhibiting the following formula (II):

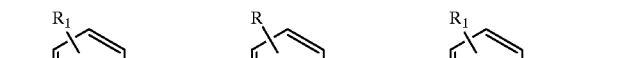

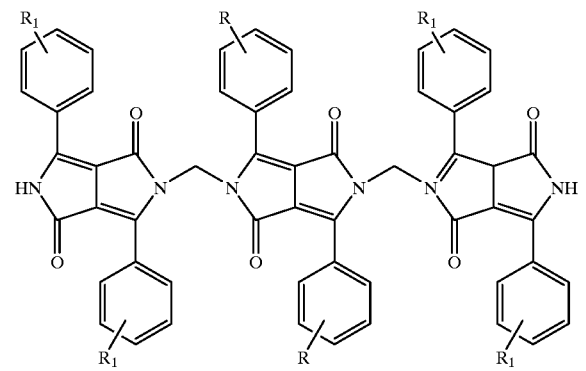

in which R and R₁ have the meanings indicated below.

| R | R₁ |
|---|---|
| H | H |
| H | Cl |
| H | CH₃ |
| H | tert-butyl |
| H | 4-phenyl |
| Cl | H |
| Cl | Cl |
| Cl | CH₃ |
| Cl | tert-butyl |
| Cl | 4-phenyl |
| CH₃ | H |
| CH₃ | Cl |
| CH₃ | CH₃ |
| CH₃ | tert-butyl |
| CH₃ | 4-phenyl |
| tert-butyl | H |
| tert-butyl | Cl |
| tert-butyl | CH₃ |
| tert-butyl | tert-butyl |
| tert-butyl | 4-phenyl |
| 4-phenyl | H |
| 4-phenyl | Cl |
| 4-phenyl | CH₃ |
| 4-phenyl | tert-butyl |
| 4-phenyl | 4-phenyl |

The preferred compound of formula (II) according to the invention is that in which $R=R_1=4$-tert-butyl.

The sulphonated derivatives of the above compounds can be prepared according to U.S. Pat. No. 5,786,487 by maintaining, through the process, a temperature greater than the temperature used to prepare the non-sulphonated derivatives, for example greater than 40° C. if a high degree of sulphonation is desired or approximately 40° C. or less if a low degree of sulphonation is desired, such as, for example, in the compound of formula (II) comprising 0.5 mol of —SO₃M.

The pigments according to the invention can advantageously be used in make-up compositions and antisun compositions, in particular colored compositions, intended for the protection of the skin and/or mucous membranes, such as the lips, without generating free radicals, and thus limit the damage to the skin and/or mucous membranes.

The pigment according to the invention can be incorporated in a cosmetic composition, in particular a make-up composition, in an amount which can be easily determined by a person skilled in the art on the basis of his general knowledge and which can range in particular from 0.01 to 50% by weight with respect to the total weight of the composition, preferably in an amount ranging from 0.5 to 25% by weight. The pigment can optionally be attached to a polymer, in particular grafted, or alternatively coated.

The composition of the invention can be provided in the form of a product to be applied to the lips, eyes, skin and/or superficial body growths. It therefore comprises a cosmetically acceptable medium, that is to say a medium compatible with all keratinous substances, such as the skin, both of the human body and of the face, the nails, the hair, the eyelashes and the eyebrows. This medium can be provided in particular in the form of an optionally thickened, indeed even gelled, suspension, dispersion or solution in an aqueous or aqueous/alcoholic solvent medium; an oil-in-water, water-in-oil or multiple emulsion; a gel or foam; an emulsified gel; a dispersion of vesicles, in particular of ionic or nonionic lipid vesicles; a two-phase or multiphase lotion; a spray; a loose, compacted or cast powder; or an anhydrous paste.

A person skilled in the art will be able to choose the appropriate form and its method of preparation on the basis of his general knowledge, taking into account, on the one hand, the nature of the constituents used, in particular their solubility in the vehicle, and, on the other hand, the application envisaged for the composition.

When the composition according to the invention is provided in the form of an emulsion, it can in addition optionally comprise a surfactant, preferably in an amount of 0.01 to 30% by weight with respect to the total weight of the composition.

According to the application envisaged, the composition can additionally comprise a film-forming polymer, such as nitrocellulose or a hydrocarbonaceous and/or silicone resin. This is in particular the case when it is desired to prepare a composition of nail-varnish, mascara or eyeliner type or a hair composition of lacquer type. The polymers can be dissolved or dispersed in the cosmetically acceptable medium and optionally used in combination with coalescence agents and/or plasticizers.

The composition according to the invention can also comprise a fatty phase composed in particular of fatty substances which are liquid at room temperature (generally 25° C.) and/or of fatty substances which are solid at room temperature, such as waxes, pasty fatty substances, gums and their mixtures.

Mention may be made, as fatty substances which are liquid at room temperature, often known as oils, which can be used in the invention, of: hydrocarbonaceous oils of animal origin, such as perhydrosqualene; vegetable hydrocarbonaceous oils, such as liquid triglycerides of fatty acids comprising 4 to 10 carbon atoms, such as triglycerides of heptanoic or octanoic acids, or sunflower, maize, soybean, grape seed, sesame, apricot, macadamia, castor or avocado oils, triglycerides of caprylic/capric acids, jojoba oil or karite butter; linear or branched hydrocarbons of mineral or synthetic origin, such as liquid paraffins and their derivatives, liquid petrolatum, polydecenes or hydrogenated polyisobutene, such as parleam; synthetic esters and ethers, in particular of fatty acids, such as, for example, purcellin oil, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates and octanoates of fatty alcohols; polyol esters, such as propylene glycol dioctanoate, neopentyl glycol diheptanoate, diethylene glycol diisononanoate and pentaerythritol esters; fatty alcohols having from 12 to 26 carbon atoms, such as octyldodecanol, 2-butyloctanol, 2-hexyldecanol, 2-undecylpentadecanol or oleyl alcohol; partially hydrocarbon-comprising and/or silicone-comprising fluorinated oils; or silicone oils, such as volatile or non-volatile and linear or cyclic polydimethylsiloxanes (PDMS) which are liquid or pasty at room temperature, such as cyclomethicones or dimethicones, optionally comprising a phenyl group, such as phenyl trimethicones, phenyltrimethylsiloxydiphenylsiloxanes, diphenylmethyldimethyltrisiloxanes, diphenyl dimethicones, phenyl dimethicones, polymethylphenylsiloxanes and their mixtures.

These oils can represent from 0 to 100% by weight with respect to the total weight of the fatty phase.

The composition according to the invention can furthermore comprise any ingredient conventionally used in the fields concerned and more especially in the cosmetic and dermatological fields. These ingredients are chosen in particular from preservatives, thickening agents for the aqueous phase (polysaccharide biopolymers, synthetic polymers) or for the fatty phase, fragrances, hydrophilic or lipophilic active principles and their mixtures. The amounts of these various ingredients are those conventionally used in the fields concerned and are, for example, from 0.01 to 20% with respect to the total weight of the composition. The nature of these ingredients and their proportions must be compatible with the production of compositions according to the invention which are stable, thickened and glossy. The composition can also comprise water at a concentration ranging from 0 to 98% of the total weight of the composition.

The composition of the invention can additionally comprise an additional particulate phase which can be present in a proportion of 0 to 35% of the total weight of the composition, preferably of 0.05 to 20%, and which can comprise pigments and/or pearlescent agents and/or fillers generally used in cosmetic compositions.

The term "pigments" should be understood as meaning white or colored and inorganic or organic particles which are insoluble in the liquid fatty phase and which are intended to color and/or opacify the composition. The term "fillers" should be understood as meaning colorless or white, inorganic or synthetic and lamellar or non-lamellar particles. The term "pearlescent agents" should be understood as meaning iridescent particles, in particular produced by certain molluscs in their shells or else synthesized. These fillers and pearlescent agents are used in particular to modify the texture of the composition.

The pigments, other than the DPP derivative, can be present in the composition in a proportion of 0 to 25% of the weight of the final composition and preferably in a proportion of 2 to 15%. Mention may be made, as inorganic pigments which can be used in the invention, of titanium, zirconium or cerium oxides, as well as zinc, iron or chromium oxides and ferric blue. Mention may be made, among the organic pigments which can be used in the invention, of carbon black and barium, strontium, calcium and aluminium lakes.

The pearlescent agents can be present in the composition in a proportion of 0 to 20% of the total weight of the composition, preferably at a level of the order of 1 to 15%. Mention may be made, among the pearlescent agents which can be used in the invention, of mica covered with titanium oxide, with iron oxide, with natural pigment or with bismuth oxychloride, such as colored titanium oxide-coated mica.

The fillers can be present in a proportion of 0 to 35% of the total weight of the composition, preferably 0.5 to 15%. Mention may in particular be made of talc, zinc stearate, mica, kaolin, nylon (in particular Orgasol) and polyethylene powders, Teflon, starch, boron nitride, microspheres formed of copolymers, such as Expancel (Nobel Industrie) or Polytrap (Dow Corning), and silicone resin microbeads (Tospearl from Toshiba, for example).

The pigment which is a subject-matter of the invention makes it possible in particular to enhance the coloring strength of the pigments which are used in combination with it and/or the goniochromatic properties of goniochromatic pigments, such as multilayer pigments or liquid crystal pigments.

The composition of the invention can advantageously comprise a solid or pasty fatty phase comprising one or more gums and/or one or more waxes. The waxes can be hydrocarbonaceous, fluorinated and/or silicone waxes and can be of vegetable, mineral, animal and/or synthetic origin. In particular, the waxes exhibit a melting temperature of greater than 25° C. and better still of greater than 45° C.

Mention may be made, as waxes which can be used in the composition of the invention, of beeswax, carnauba or candelilla wax, paraffin wax, microcrystalline waxes, ceresin or ozokerite; or synthetic waxes, such as polyethylene or Fischer-Tropsch waxes or silicone waxes, such as alkyl or alkoxy dimethicones having from 16 to 45 carbon atoms.

The gums are generally high molecular weight PDMSs and the pasty substances are generally hydrocarbonaceous compounds, such as lanolins and their derivatives, or PDMSs.

The natures and the amounts of the solid substances depend on the mechanical properties and textures desired. By way of indication, the composition can comprise from 0 to 50% by weight of waxes with respect to the total weight of the composition and better still from 5 to 30%.

The composition according to the invention can also comprise one or more cosmetically acceptable organic solvents (acceptable tolerance, toxicology and feel). These organic solvents can represent from 0% to 98% of the total weight of the composition and can be chosen from the group consisting of hydrophilic organic solvents, lipophilic organic solvents, amphiphilic solvents or their mixtures.

Mention may be made, among hydrophilic organic solvents, of, for example, linear or branched lower monoalcohols having from 1 to 8 carbon atoms, polyols, mono- or dialkyl isosorbides, the alkyl groups of which have from 1 to 5 carbon atoms, glycol ethers or fatty esters.

This composition can have the appearance of a powder, cream, ointment, fluid lotion, soft paste, salve, or cast or moulded solid, in particular as a stick or in a dish.

The composition according to the invention can advantageously be used for making up the skin and/or lips and/or superficial body growths, according to the nature of the constituents used. In particular, the composition of the invention can be a lipstick or a lip gloss which can be used as such or for applying to a lipstick film, in particular for enhancing its gloss and/or color (topcoat). It can also constitute a nail varnish, a foundation, an eye-circle concealer, or an eye-outlining product, an eyeliner, a mascara, an eyeshadow, a powder, a blusher or a make-up for the body. These compositions can additionally comprise cosmetic or dermatological active principles for the purpose in particular of contributing a care or treating aspect to the composition. Thus, the composition can comprise vitamins and other lipophilic active principles (lanolin, UVA screening agent) or hydrophilic active principles (moisturizers, such as glycerol).

More specifically, a subject-matter of the invention is a lip product or a blusher.

The composition of the invention is more particularly provided in anhydrous form.

The composition of the invention can be obtained by heating the various constituents to the highest melting temperature of the waxes and then pouring the molten mixture into a mould (dish or glove-finger). It can also be obtained by extrusion , as disclosed in Application EP-A-667,146.

A further subject-matter of the invention is a cosmetic use of the above composition for caring for and/or making up and/or protecting the skin and/or lips and/or superficial body growths and a use of this composition for preparing a salve intended to treat and/or protect the skin and/or lips. Another subject-matter of the invention is a process for the cosmetic treatment of the skin and/or lips and/or superficial body growths which consists in applying the composition defined above to the skin and/or lips and/or superficial body growths.

A further subject-matter of the invention is the use, in a colored cosmetic composition, of a coloring agent as described above in order to protect the skin and/or lips and/or superficial body growths against the damaging effects of free radicals and/or to combat cutaneous signs of ageing, in particular photoinduced ageing. These signs of ageing are in particular wrinkles, fine lines or flaccid and/or yellowed skin.

A further subject-matter of the invention is a process for the cosmetic protection of the skin and/or lips and/or superficial body growths against the damaging effects of free radicals and/or for combating cutaneous signs of photoinduced ageing, which consists in applying the composition as defined above to the skin and/or lips and/or superficial body growths.

The composition examples below are given by way of illustration.

EXAMPLE 1

Lipstick

| | |
|---|---|
| Polyethylene wax | 14 g |
| Sesame oil | 78 g |
| Pigment derived from DPP of formula (II) in which R = $R_1$ = 4-tert-butyl | 5 g |
| Titanium dioxide | 3 g |

Method of Preparation:

homogenization of the oil+pigments mixture for 45 minutes in an oil bath, passing the mixture 3 times in succession through a triple roll mill, homogenization of the oil+pigments mixture for 30 minutes in an oil bath, moulding in a mould at 42° C. and 30 minutes in a freezer.

A lipstick is obtained which has an intense orange color, has high coverage, is glossy, is stable to light and leaves no mark after it has been removed.

EXAMPLE 2

Blusher

| | |
|---|---|
| Talc | 38 g |
| Mica | 20 g |
| Bismuth oxychloride | 8 g |
| Zinc stearate | 3 g |
| Nylon powder | 20 g |
| Pigment derived from DPP of formula (II) in which R = $R_1$ = 4-tert-butyl | 5 g |
| Fatty binder (*) | q.s. for 100 g |

(*) Mixture of carbonaceous 0113 comprising:
3.6 g of capric/caprylic acid triglycerides,
2.0 g of hydrogenated isoparaffin (non volatile),
1.0 g of jojoba oil.

Method of Preparation:

premixing all the fillers and pigments, 5 minutes with a Lödige device (powder mixer/homogenizer), addition of the organic binder, 5 minutes with a Lödige device, air jet milling (Chrispro), sieving at 160 microns.

EXAMPLE 3

Lip Lacquer

| | | |
|---|---|---|
| Aqueous dispersion of acrylic/styrene polymer (Neocryl A-1052 from Zeneca) | 20.0 g | active material |
| Tributyl acetylcitrate | 2.5 g | |
| Bismuth vanadate | 1.5 g | |
| Derivative of DPP of formula (II) in which R = R = 4-tert-butyl | 1.5 g | |
| Glycerol | 1.25 g | |
| Water | q.s. for 100 g | |

Method of Preparation:

The tributyl acetylcitrate, the pigments and the aqueous phase (glycerol+water) are added at room temperature to the polymer dispersion and then the mixture is homogenized.

A lip lacquer is obtained which has an orange color, is stable and is covering.

What is claimed is:

1. Coloured cosmetic composition for topical application, consisting essentially of a cosmetically acceptable medium and a pigment of formula (I)

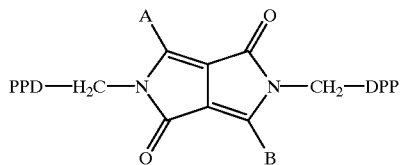

(I)

in which A and B are identical or different aryl radicals and DPP is a diketodiarylpyrrolopyrrolidyl radical, the pigment of formula (I) being substituted by 0 to 6 mol of —$SO_3M$ per mole of pyrrolopyrrole derivative, M being a hydrogen atom or a metal or ammonium cation.

2. Composition according to claim 1, wherein DPP is a 1,4-diketo-3,6-diarylpyrrolo[3,4-c]pyrrolidyl radical of formula:

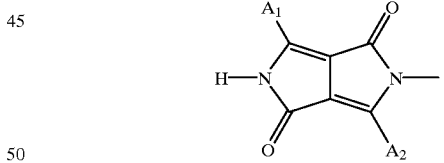

in which $A_1$ and $A_2$ are identical or different aryl radicals.

3. Composition according to claim 1 wherein A and B are radicals of formulae:

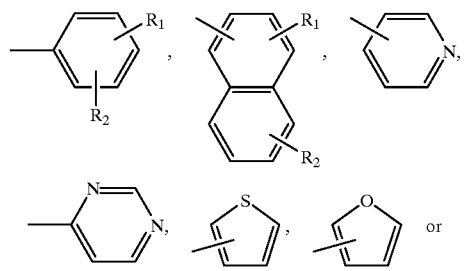

-continued

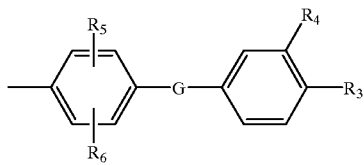

in which:

R₁ and R₂ denote, independently of one another, a hydrogen or halogen atom or a $C_1$–$C_{18}$ alkyl, $C_1$–$C_{18}$ alkoxy, $C_1$–$C_{18}$ alkylmercapto, $C_1$–$C_{18}$ alkylamino, $C_1$–$C_{18}$ alkoxycarbonyl, $C_1$–$C_{18}$ alkylaminocarbonyl, —CN, —NO₂, trifluoromethyl, $C_5$–$C_6$ cycloalkyl, —HC=N—($C_1$–$C_{18}$ alkyl), phenyl,

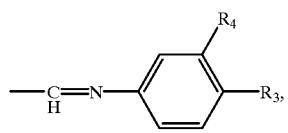

imidazoly, pyrazolyl, triazolyl, piperazinyl, pyrrolyl, oxazolyl, benzoxazolyl, benzothiazolyl, benzimidazolyl, morpholinyl, piperidinyl or pyrrolidinyl radical, G denotes —CH₂—, —CH(CH₃)—, —C(CH₃)₂—, —CH=N—, —N=N—, —O—, —S—, —SO—, —SO₂—, —CONR— or —NR₇—, R₃ and R₄ denote, independently of one another, a hydrogen or halogen atom or a $C_1$–$C_6$ alkyl, $C_1$–$C_{18}$ alkoxy or —CN radical, R₅ and R₆ denote, independently of one another, a hydrogen or halogen atom or a $C_1$–$C_6$ alkyl radical, and R₇ is a hydrogen atom or a $C_1$–$C_6$ alkyl radical.

4. Composition according to claim 2 wherein A, B, A₁ and A₂ are radicals of formulae:

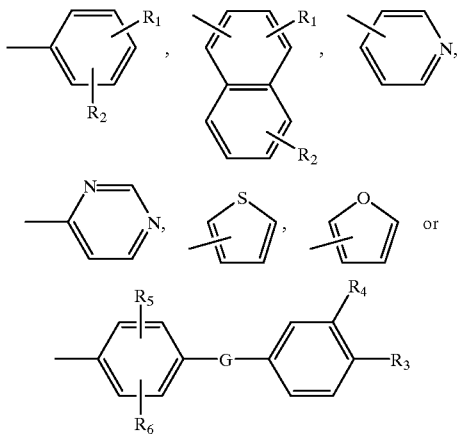

in which:

R₁ and R₂ denote, independently of one another, a hydrogen or halogen atom or a $C_1$–$C_{18}$ alkyl, $C_1$–$C_{18}$ alkoxy, $C_1$–$C_{18}$ alkylmercapto, $C_1$–$C_{18}$ alkylamino, $C_1$–$C_{18}$ alkoxycarbonyl, $C_1$–$C_{18}$ alkylaminocarbonyl, —CN, —NO₂, trifluoromethyl, $C_5$–$C_6$ cycloalkyl, —HC=N—($C_1$–$C_{18}$ alkyl), phenyl,

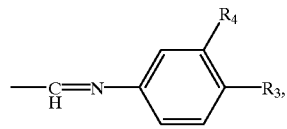

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl radical, G denotes —CH₂—, —CH(CH₃)—, —C(CH₃)₂—, —CH=N—, —N=N—, —O—, —S—, —SO—, —SO₂—, —CONR— or —NR₇—, R₃ and R₄ denote, independently of one another, a hydrogen or halogen atom or a $C_1$–$C_6$ alkyl, $C_1$–$C_{18}$ alkoxy or —CN radical, R₅ and R₆ denote, independently of one another, a hydrogen or halogen atom or a $C_1$–$C_6$ alkyl radical, and R₇ is a hydrogen atom or a $C_1$–$C_6$ alkyl radical.

5. Composition according to claim 3, wherein A and B denote a group of formula:

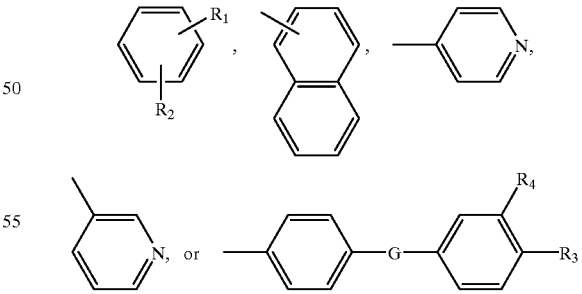

in which R₁ and R₂ each denote, independently of one another, a hydrogen, chlorine or bromine atom or a $C_1$–$C_4$ alkyl, $C_1$–$C_6$ alkoxy, $C_1$–$C_6$ alkylamino, phenyl or —CN radical, G denotes —O—, —NR₇—, —N=N— or —SO₂—, R₃ and R₄ denote a hydrogen atom, and R₇ is a hydrogen atom or a methyl or ethyl radical.

6. Composition according to claim 4, wherein A, B, A₁ and A₂ denote a group of formula:

in which R₁ and R₂ each denote, independently of one another, a hydrogen, chlorine or bromine atom or a $C_1$–$C_4$ alkyl, $C_1$–$C_6$ alkoxy, $C_1$–$C_6$ alkylamino, phenyl or —CN radical, G denotes —O—, —NR₇—, —N=N— or SO₂—, R₃ and R₄ denote a hydrogen atom, and R₇ is a hydrogen atom or a methyl or ethyl radical.

7. Composition according to claim 5, wherein A and B denote a group of formula:

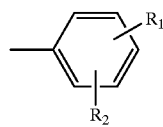

in which $R_1$ and $R_2$ each denote, independently of one another, a hydrogen, chlorine or bromine atom or a methyl, tert-butyl, phenyl or —CN radical.

8. Composition according to claim 6, wherein A, B, $A_1$ and $A_2$ denote a group of formula:

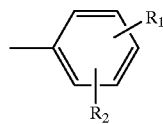

in which $R_1$ and $R_2$ each denote, independently of one another, a hydrogen, chlorine or bromine atom or a methyl, tert-butyl, phenyl or —CN radical.

9. Composition according to claim 7, wherein at least one of the $R_1$ and $R_2$ radicals denotes hydrogen.

10. Composition according to claim 8, wherein at least one of the $R_1$ and $R_2$ radicals denotes hydrogen.

11. Composition according to claim 7, wherein at least one of the $R_1$ and $R_2$ radicals denotes hydrogen and the other is in the 3- or 4-position of the phenyl nucleus.

12. Composition according to claim 8, wherein at least one of the $R_1$ and $R_2$ radicals denotes hydrogen and the other is in the 3- or 4-position of the phenyl nucleus.

13. Composition according to claim 7, wherein A and B are identical and are selected from the group consisting of phenyl, 4-methylphenyl, 4-tert-butylphenyl, 4-chlorophenyl, 4-bromophenyl and biphenyl-1-yl radicals.

14. Composition according to claim 8, wherein A and B are identical and are selected from the group consisting of phenyl, 4-methylphenyl, 4-tert-butylphenyl, 4-chlorophenyl, 4bromophenyl and biphenyl-1-yl radicals.

15. Composition according to claim 8, wherein $A_1$ and $A_2$ are identical and are selected from the group consisting of phenyl, 4-methylphenyl, 4-tert-butylphenyl, 4-chlorophenyl, 4-bromophenyl and biphenyl-1-yl radicals.

16. Composition according to claim 7, wherein A and B are identical and are selected from the group consisting of phenyl, 4-tert-butylphenyl and 4-methylphenyl radicals.

17. Composition according to claim 8, wherein $A_1$ and $A_2$ each denote a 4-tert-butylphenyl radical and A and B are identical and are selected from the group consisting of phenyl, 4-tert-butylphenyl and 4-methylphenyl radicals.

18. Composition according to claim 16, wherein A and B each denote a 4-tert-butylphenyl radical.

19. Composition according to claim 17, wherein $A_1$, $A_2$, A and B each denote a 4-tert-butylphenyl radical.

20. Composition according to claim 8, wherein $A_1$ and $A_2$ each denote a 4-methylphenyl radical and A and B are identical and are selected front the group consisting of phenyl, 4-tert-butylphenyl and 4-methylphenyl radicals.

21. Composition according to claim 20, wherein $A_1$ and $A_2$ each denote a 4-methylphenyl radical and A and B are identical and each denote a 4-tert-butylphenyl radical.

22. Composition according to claim 21 wherein the pigment of formula (I) is substituted by 0 to 2 mol of —SO$_3$M per mole.

23. Composition according to claim 22 wherein the pigment of formula (I) does not comprise an —SO$_3$M substituent.

24. Composition according to claim 22, wherein the pigment of formula (I) comprises 0.5 mol of —SO$_3$M per mole.

25. Composition according to claim 1, wherein the metal cation M is a sodium, potassium or lithium cation.

26. Composition according to claim 1 wherein the pigment of formula (I) is present in a proportion of 0.01 to 50% by weight with respect to the total weight of the composition.

27. Composition according to claim 26, wherein the pigment of formula (I) is present in a proportion of 0.5 to 25% by weight with respect to the total weight of the composition.

28. Composition according to claim 1 in the form of a product for making up at least one of human skin, lips, and superficial body growths.

29. Composition according to claim 1, in the form of a nail varnish, mascara, eyeliner, lipstick, lip gloss, foundation, eye-circle concealer, blusher, eye-outlining product, eyeshadow, powder or make-up for the body.

30. Coloured cosmetic composition for topical application, consisting essentially of a cosmetically acceptable medium and a pigment of formula (I)

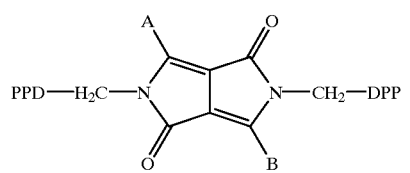

(I)

in which A and B are identical or different aryl radicals and DPP is a diketodiarylpyrrolopyrrolidyl radical, the pigment of formula (I) being substituted by 0 to 6 mol of —SO$_3$M per mole of pyrrolopyrrole derivative, M being a hydrogen atom or a metal or ammonium cation, and at least one fatty phase selected from the group consisting of oils, waxes, gums, pasty fatty substances and their mixtures.

31. Coloured cosmetic composition for topical application, consisting essentially of a cosmetically acceptable medium and a pigment of formula (I)

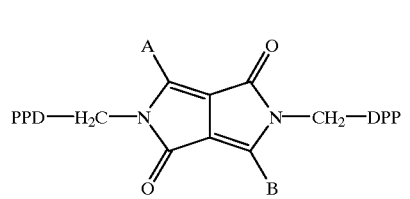

(I)

in which A and B are identical or different aryl radicals and DPP is a diketodiarylpyrrolopyrrolidyl radical, the pigment of formula (I) being substituted by 0 to 6 mol of —SO$_3$M per mole of pyrrolopyrrole derivative, M being a hydrogen atom or a metal or ammonium cation, and a particulate phase selected from the group consisting of inorganic pigments, carbon black, barium, strontium, calcium and aluminum lakes, pearlescent agents and fillers, which is optionally present in a proportion of 0 to 35% of the total weight of the composition.

32. Composition according to claim 1, in anhydrous form.

33. A method of at least caring for, making up and protecting the skin, lips, or superficial body growths comprising applying a composition of claim 1 to said skin, lips or superficial body growth.

34. A method of preparing a salve intended to treat or protect the skin or lips comprising mixing a composition of claim 1, with a salve base.

35. Process for the cosmetic protection of the skin, lips or superficial body growths against the damaging effects of free radicals or for combating cutaneous signs of photoinduced ageing, comprising applying the composition according to claim 1 to the skin, lips or superficial body growths.

* * * * *